(12) United States Patent
Schierschmidt et al.

(10) Patent No.: US 10,206,339 B2
(45) Date of Patent: Feb. 19, 2019

(54) INDICATING OF UNSHARP TEETH AT A DISC SAW BY MEASURING OF SPEED OF ROTATION

(71) Applicant: Komatsu Forest AB, Umeå (SE)

(72) Inventors: William Schierschmidt, Chattanooga, TN (US); Peter Assarsson, Umeå (SE)

(73) Assignee: Komatsu Forest AB, Umeå (SE)

( * ) Notice: Subject to any disclaimer, the term of this patent is extended or adjusted under 35 U.S.C. 154(b) by 129 days.

(21) Appl. No.: 15/103,790

(22) PCT Filed: Dec. 20, 2013

(86) PCT No.: PCT/SE2013/051611
§ 371 (c)(1),
(2) Date: Jun. 10, 2016

(87) PCT Pub. No.: WO2015/094073
PCT Pub. Date: Jun. 25, 2015

(65) Prior Publication Data
US 2016/0309666 A1    Oct. 27, 2016

(51) Int. Cl.
| | | |
|---|---|---|
| *A01G 23/091* | (2006.01) |
| *A01G 23/08* | (2006.01) |
| *B23D 47/12* | (2006.01) |
| *B27B 5/10* | (2006.01) |
| *B23D 59/00* | (2006.01) |
| *G01N 3/58* | (2006.01) |

(52) U.S. Cl.
CPC ........... *A01G 23/091* (2013.01); *A01G 23/08* (2013.01); *B23D 47/12* (2013.01); *B23D 59/001* (2013.01); *B27B 5/10* (2013.01); *G01N 3/58* (2013.01)

(58) Field of Classification Search
CPC ....... A01G 23/09; A01G 23/08; A01G 23/091
USPC ........................................................ 73/104
See application file for complete search history.

(56) References Cited

U.S. PATENT DOCUMENTS 4,039,010 A    8/1977    Tucek
4,738,291 A    4/1988    Isley

FOREIGN PATENT DOCUMENTS

DE    102011005317 A1    9/2012
WO    03096794 A1    11/2003

OTHER PUBLICATIONS

International Search Report received for PCT Patent Application No. PCT/SE2013/051611, dated Jun. 25, 2015, 4 pages.
International Preliminary Report on Patentability received for PCT Application No. PCT/SE2013/051611, dated Jun. 30, 2016, 6 pages.
International Written Opinion received for PCT Application No. PCT/SE2013/051611, dated Sep. 4, 2014, 4 pages.

*Primary Examiner* — John Fitzgerald
*Assistant Examiner* — Rodney T Frank
(74) *Attorney, Agent, or Firm* — Morrison & Foerster LLP

(57) ABSTRACT

The present invention concerns a method for the indication of the sharpness of the teeth at a harvesting head at a forestry machine, an arrangement for the execution of the method, and a forestry machine for the use of the arrangement during execution of the method.

11 Claims, 2 Drawing Sheets

INDICATING OF UNSHARP TEETH AT A DISC SAW BY MEASURING OF SPEED OF ROTATION

CROSS-REFERENCE TO RELATED APPLICATION

This application is a U.S. National Stage patent application of PCT/SE2013/051611 filed on Dec. 20, 2013, the entire contents of which are incorporated herein by reference.

TECHNICAL AREA

The present invention concerns a tree-felling working head at a forestry machine, to be more precise, an arrangement and a method for indicating when the teeth of the working head are too blunt and therefore need to be sharpened or exchanged.

BACKGROUND

In large forestry plantations in, for example, South America and Australia, forestry stands grow in which the trees demonstrate a relatively uniform size and with equivalent properties such as density and moisture content. The trees grow rapidly and are planted in rows such that they grow with equal spaces at a separation from each other and on relatively level ground. These conditions make efficient forestry possible in which one or several forestry machines can work along the outer edge of the stand and process the trees at a rapid pace.

The processing often takes place with the aid of accumulating working heads arranged at an arm of a tool carrier in the form of a forestry machine, excavator or similar that is driven by wheels or tracks. The head is attached to the arm by a tool fixture of known type in a manner that allows it to be removed. The term "accumulating working head" is here used to denote a timber working head that is manoeuvred by the arm of the tool carrier to a first tree, the tree is clamped against it by one or several holder arms, and cut by a rotating toothed blade or disc. The working head is subsequently moved to the next tree, which also is clamped against the working head and cut. This continues until the working head is full. When the working head is full, the arm is pivoted away from the working area and deposits the collected bundle of cut trees, after which the procedure is repeated.

The blade or disc of the working head comprises a flywheel with a large mass and with teeth arranged along the periphery of the disc. The disc is accelerated by a motor up to a pre-determined speed before the cutting, after which the cutting is started. It is indicated that the correct speed has been reached by a gauge of the rate of revolution or by a pressure gauge arranged in connection with the disc or the motor. This gauge of the rate of revolution is used also to indicate when the speed of rotation is too low for it to be possible to carry out efficient cutting. As a consequence of the uniform properties and sizes of the trees, it is possible to cut a tree in a very short time, approximately one second or less. When a number of trees have been cut, a waiting period occurs in order for the disc to be able to reach again the correct speed.

The disadvantage of the prior art technology is that when the teeth of the disc loose their sharpness and become blunt after a number of cuttings, the consumption of time for each cutting becomes longer. This means that the working head cannot be filled with trees before the disc must be accelerated up to the correct speed again, whereby the efficiency becomes lower.

Monitoring of the sharpness of the teeth is currently carried out by the driver, who sits in the forestry machine. Not only does production of heat take place when the teeth are blunt and must wear their way through the trunk, but also the driver discovers that the speed of the disc becomes too low before the working head is filled.

SUMMARY OF THE INVENTION

The disadvantages described above are solved through an arrangement and a method for the indication of when the teeth of the disc are too blunt and must be exchanged or sharpened, without it being necessary for the driver to observe the consumption of time during cutting and the degree of filling of the accumulating working head.

DESCRIPTION OF EMBODIMENTS

Figure 2:
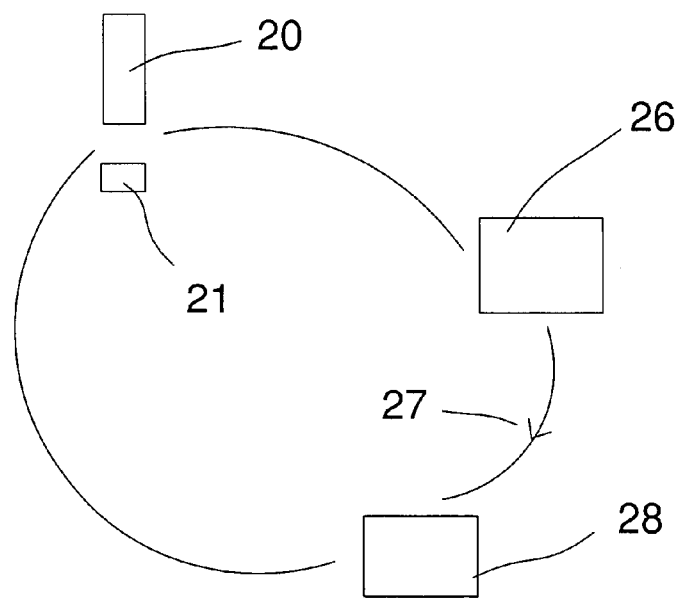
FIG. 2 shows a block diagram of signal pathways.
Figure 1:
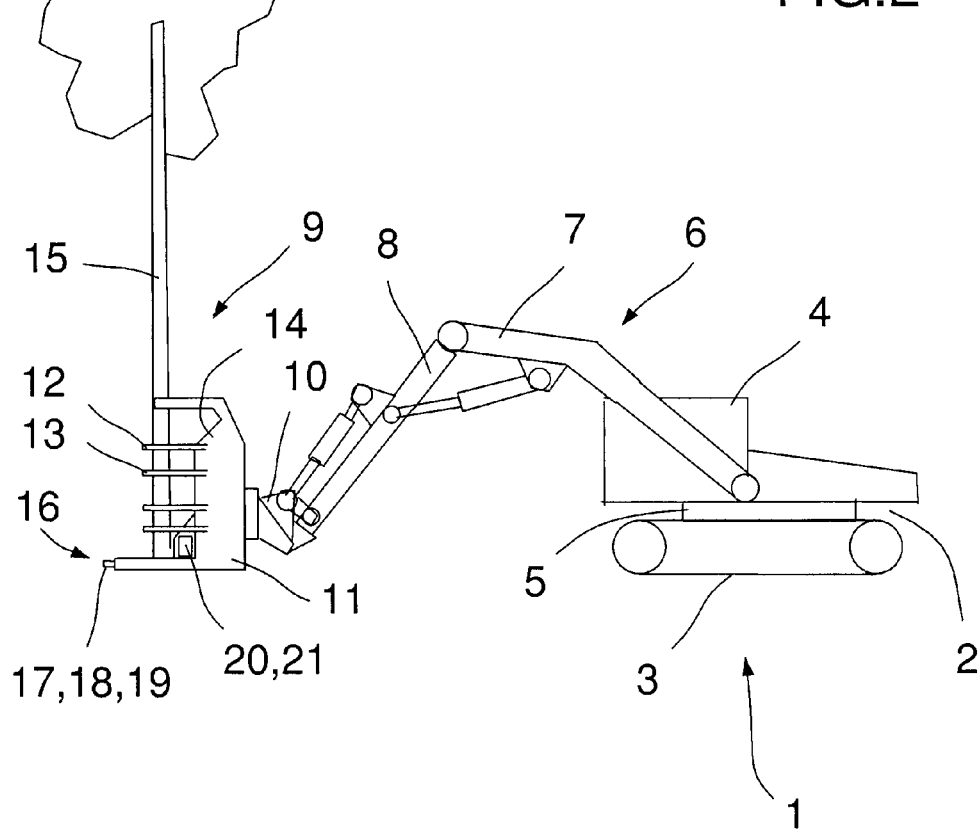
FIG. 1 shows schematically a forestry machine with an accumulating working head.

FIG. 1 shows a forestry machine 1 in the form of a tracked tool carrier. It comprises a chassis 2 with tracks 3 on each side. A driver's cabin 4 is located such that it can be rotated on a slewing ring 5 and can be rotated through 360 degrees. A folding arm 6 is mounted jointed at the chassis 2 and it comprises in known manner a boom 7 and a stick 8, which are mounted jointed relative to each other. A hydraulic system with hydraulic cylinders, lines, valves and pumps drives in known manner the driving of the tracks 3, regulation of the driver's cabin 4 and manoeuvring of the arm 6. At the farthest end of the arm 6 a tree harvesting head 9 is attached at a tool fixture 10, advantageously in a manner that allows it to be removed. The tree harvesting head may in another embodiment be directly attached to the arm.

The tree harvesting head 9 comprises an extended frame 11 with at least one holder arm 12 and one grip arm 13. An accumulation compartment 14 that extends in the longitudinal direction of the frame has been made in the frame for the accumulation of cut trees. The term "holder arm" 12 is here used to denote an arm that can be regulated in a manner that can hold a sawn tree 15 fixed against the frame 11. The term "grip arm" 13 is here used to denote a similar arm, although this arm is jointed. When the arm 13 grips a tree 15, it is clamped against the frame 11, after which the tree 15 is cut. The subsequent tree is clamped against the grip arm 13, and the grip arm is able, due to the fact that it is jointed, to slide out between the two trees such that both of the trees are held fixed by the holder arm 12. A certain number of trees can be gripped and held fixed in the manner that is described above, until the accumulation compartment 14 is full. The filling of an accumulation compartment 14 with cut trees will be denoted below by the term "accumulation sequence A".

The end of the frame 11 that faces the ground is arranged with a cutting arrangement 16. The cutting arrangement comprises a rotating disc 17 or a flywheel with a large mass. The disc 17 is provided with fixed or removable teeth 18 along the periphery 19 of the disc 17. The large mass of the disc 17 ensures that the speed of rotation of the disc is influenced to a lesser degree than if, for example, a saw blade had been used.

The disc 17 is driven by a motor 20, and it is an advantage if this is carried out by direct driving through a hydraulic motor. It is an advantage if the motor 20 is driven by the hydraulic system of the forestry machine 1. The motor 20 is arranged inside the frame 11 of the working head 9 and is in this way protected from external influence by tree trunks that are held against the frame 11. The motor 20 is provided with a speed sensor 21 for the direct measurement and registration of the speed of rotation of the motor. The speed sensor 21 may in another embodiment be located in connection with the periphery 19 of the disc 17 for the measurement of the speed of rotation. The speed sensor 21 is so arranged that it measures and registers the speed of rotation of the disc 17. Since the mass of the disc 17 is so great, the inertia of the disc can be used during the cutting of trees. Before each accumulation sequence A, the speed of rotation of the disc is increased to a pre-determined value 22. Such an increase in the speed will be denoted below by the term "recovery phase B".

At each cutting, the disc 17 is exposed to a resistance that leads to a reduction in the speed of rotation of the disc. Even though the motor 20 and the hydraulic system strive to maintain the speed of rotation of the disc 17 at a pre-determined value 22 by imparting a small increase in speed after each cutting, this increase is less than the reduction in the speed of rotation that the disc 17 experiences during each cutting.

Figure 3:
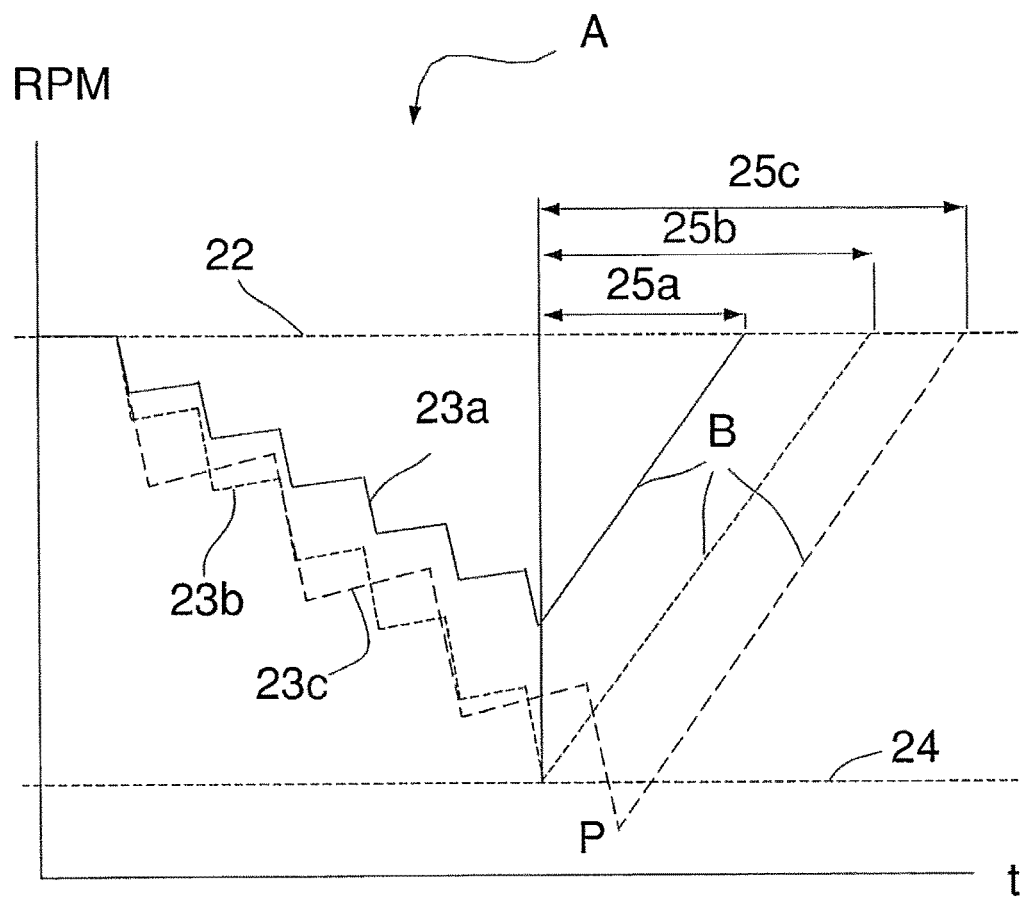
FIG. 3 shows a diagram of an accumulation sequence with sharp and blunt teeth, and it shows when indication takes place and the teeth need to be exchanged or sharpened.

The resistance is equal at each tree, due to the uniform properties of the stand of trees. This allows statistical results of the number of cuttings to be used in order to discover when the resistance at each tree has become too large. A diagram of an accumulation sequence A is shown in FIG. 3, where the cutting is initiated when the disc 17 has achieved a pre-determined speed 22, which has been measured and registered. Each tree that is cut leads to blunter teeth and gives a reduction in the speed of rotation. This reduction in the speed of rotation becomes greater as the teeth become blunter, and it is measured and registered, as is illustrated in FIG. 3 with the reference numbers 23*a*, 23*b* and 23*c*, where 23*a* is the reduction in the speed of rotation when the teeth are sharp, 23*b* is the reduction in the speed of rotation when the teeth are blunt, and 23*c* is the reduction in the speed of rotation that leads to insufficient time being available in which to fill the accumulation compartment 14. When a number of cuttings, which in this embodiment is six cuttings, has been carried out, the reductions 23*a*-23*c* in the speed of rotation of the disc have been added and registered in order finally to become so large that a lowest permissible speed of rotation 24 has been registered, whereby a recovery phase B is initiated during a period of time that is denoted in FIG. 3 with the reference numbers 25*a*-25*c*. The speed of rotation 22 that the disc has before an accumulation sequence A is initiated must be sufficient to carry out the number of cuttings that is required to fill the accumulation compartment 14, i.e. the speed of the disc must be higher than the lowest permissible speed of rotation 24 when all reductions in the speed of rotation have been subtracted from the original speed 22. If the recovery phase B must be initiated before the accumulation compartment has been filled, in this embodiment after four cuttings as is shown in FIG. 3 with the reference symbol P, this means that the reduction in speed of rotation 23*c* is too high, and this in turn indicates that the teeth 18 of the disc 17 are too blunt, whereby a signal 27 is transmitted to the driver. This is illustrated in FIG. 3 with the reference number 25*c*. The recovery phase B can be described as the working head 9 being held at a distance greater than the cutting distance from the tree 15 after the final tree in an accumulation sequence has been cut, while the motor 20 is allowed to work in order to increase the speed of rotation to the pre-determined speed 22, and it is an advantage if this takes place during the period 25*a*-25*c* during which the working head 9 is being emptied. The speed of rotation 22 is determined by the diameter of the disc in such a manner that a disc with a lower diameter can be given a higher pre-determined speed of rotation and a disc with a larger diameter can be given a lower pre-determined speed of rotation.

If the working head 9 can be filled without the need for a recovery phase B arising, it may however be the case that the recovery phase will be too long, i.e. that the time 25*b* from the final cutting having been carried out until the working head has again been returned to a tree and the speed of rotation 22 has been registered. This means that the speed of rotation has been reduced by too great an amount and that the teeth have reached their maximal capacity and are on the verge of needing sharpening or being exchanged, whereby a signal 27 is transmitted to the driver.

When the resistance at each tree becomes too great, for example at the point P in FIG. 3, and the accumulation compartment 14 of the working head 9 cannot be filled between two recovery phases B, this indicates that the teeth 18 of the disc 17 are blunt. This means that the driver must allow a recovery phase B to take place, without having filled the accumulation compartment 14. This leads to a large loss of time and an inefficient working procedure. In order to avoid this, statistics are retrieved for each tree 15 that is cut during the initial work cycle C. The term "work cycle" is here used to denote the time from the first cutting until the last of a pre-determined number of bundles has been placed on the ground, i.e. a number of accumulation sequences A carried out as shown in FIG. 3. The values that are registered and collected are the speed of rotation after each cut tree, the consumption of time and the resistance in the form of an increase in pressure in the hydraulic system, which leads to a reduction 23 in the speed of rotation. These collected values are stored in a memory of a calculation computer 26 to which the speed sensor 21 is connected. Also data concerning the properties of the working head 9 are stored in the memory, for example the number of trees that can be accommodated in the accumulation compartment 14, the sizes and the capacities of the motor 20 and the hydraulic pump, when the teeth 18 of the disc 17 were sharpened or exchanged, and data concerning the relevant forestry stand that is being processed such as the estimated mean diameter and density.

Signals 27 that indicate that the teeth are blunt or need to be exchanged are sent through the calculation computer 26 to a display 28 inside the driver's cabin, which makes it possible for the driver to plan maintenance, such as sharpening or the exchange and teeth.

The present invention is not limited to what has been described above and shown in the drawings: it can be changed and modified in several different ways within the scope of the innovative concept defined by the attached patent claims.

The invention claimed is:

1. A method for indication of sharpness of teeth at a harvesting head at a forestry machine during operation in a forestry stand with essentially uniform properties of its trees, which harvesting head comprises a cutting arrangement of a type that comprises a disc that rotates at a variable speed and that is provided with teeth, and an accumulation compartment for accumulation of cut trees, the method comprising the steps:

a) initiating an accumulation sequence with a highest permissible and a lowest permissible speed of rotation of the disc, and an accumulation compartment capacity value being stored in a memory at a processing unit;

b) increasing the speed of the disc until the highest permissible speed of rotation of the disc is registered;

c) maneuvering and placing the working head against a tree, after which the tree is cut, wherein at each cutting, the disc is exposed to a resistance that leads to a reduction in the speed of the rotation of the disc, wherein the reduction of speed of rotation increases as the teeth become more blunt;

d) registering a reduction of the speed of rotation of the disc during the cutting and subtracting the reduction of the speed of rotation of the disc during the cutting from the speed in b), e) filling the accumulation compartment by repeating the steps c) to d); and f) in accordance with a determination that the speed of rotation of the disc reaches the lowest permissible speed before the accumulation compartment has reached the accumulation compartment capacity value, transmitting, to a driver, a signal indicating that the teeth of the disc are too blunt.

2. The method according to claim 1, further comprising the steps after step e) if step f) does not occur:

g) raising the speed of rotation of the disc during the period in which the working head is maneuvered to a position at which the accumulation compartment is emptied;

h) maneuvering the working head in a direction towards a tree before it is cut;

i) initiating an accumulation sequence through the speed of rotation of the disc being registered and compared with the registration in b);

j) transmitting a signal if the speed of rotation in step i) is lower than the speed in step b); and k) in accordance with a determination that the registration in step i) corresponds to the registration in step b), repeating the feat steps c) to d).

3. The method according to claim 2, whereby the signals in steps f) and j) indicate that the teeth of the disc are too blunt and need to be exchanged or sharpened.

4. The method according to claim 2, whereby the registrations and the signals in steps a) to j) are stored and processed in a processing unit.

5. The method according to claim 4, whereby the processing unit compares the registrations from each accumulation sequence and transmits a signal if the reduction of the speed of rotation in step d) when the accumulation compartment has been filled approaches the pre-determined lowest permissible speed of rotation, or if the time required for the increase of the speed of rotation up to the speed in step a) is longer than the time that is required to carry out steps g) and h).

6. The method according to claim 2, whereby the signals in steps f) and j) are indicated on a display that is visible to the driver of the forestry machine.

7. An arrangement for indication of sharpness of teeth at a forestry machine during operation in a forestry stand with essentially uniform properties of its trees, the arrangement comprising:

a harvesting head comprising a cutting arrangement of a type that comprises a disc that rotates at a variable speed and that is provided with teeth;

an accumulation compartment for accumulation of cut trees; and a sensor that registers the speed of rotation of the disc after each tree cutting, wherein at each cutting, the disc is exposed to a resistance that leads to a reduction in the speed of the rotation of the disc, wherein the reduction of speed of rotation increases as the teeth become more blunt, and wherein in accordance with a determination that the speed of rotation of the disc reaches a lowest permissible speed before an accumulation compartment capacity value has been reached, a signal indicating that the teeth of the disc are too blunt is transmitted.

8. The arrangement according to claim 7, further comprising a calculation computer to which the registrations of the sensor are transmitted and compared with a predetermined lowest permissible speed.

9. The arrangement according to claim 8, further comprising a display for the reception of a signal that is transmitted from the calculation unit when the lowest permissible speed has been reached.

10. A working head configured to be used during cutting and accumulation of trees, comprising a frame at which a disc that is driven by a motor and that is provided with teeth is mounted, where the working head comprises a speed sensor for indication of sharpness of the teeth according to claim 1.

11. A forestry machine comprising a working head according to claim 10.

* * * * *